US008126535B2

(12) United States Patent
Maier et al.

(10) Patent No.: US 8,126,535 B2

(45) Date of Patent: Feb. 28, 2012

(54) MARKER NAVIGATION SYSTEM FOR DETECTING AND DISPLAYING THE LOCATION OF MARKER MEANS

(75) Inventors: Christian Maier, München (DE); Jörg Uhde, München (DE); Manfred Weiser, München (DE)

(73) Assignee: Brainlab AG, Feldkirchen (DE)

(*) Notice: Subject to any disclaimer, the term of this patent is extended or adjusted under 35 U.S.C. 154(b) by 1168 days.

(21) Appl. No.: 11/873,508

(22) Filed: Oct. 17, 2007

(65) Prior Publication Data

US 2008/0154125 A1 Jun. 26, 2008

Related U.S. Application Data

(60) Provisional application No. 60/862,070, filed on Oct. 19, 2006.

(30) Foreign Application Priority Data

Oct. 17, 2006 (EP) .................................... 06021696

(51) Int. Cl.
*A61B 5/05* (2006.01)

(52) U.S. Cl. ......... 600/424; 600/425; 600/426; 606/130

(58) Field of Classification Search .................. 600/424, 600/426; 606/130

See application file for complete search history.

(56) References Cited

U.S. PATENT DOCUMENTS

| | | | | |
|---|---|---|---|---|
| 5,921,992 | A | 7/1999 | Costales et al. | |
| 6,351,659 | B1 | 2/2002 | Vilsmeier | |
| 6,466,815 | B1 | 10/2002 | Saito et al. | |
| 6,711,431 | B2 * | 3/2004 | Sarin et al. | 600/426 |
| 7,634,306 | B2 * | 12/2009 | Sarin et al. | 600/426 |
| 7,780,681 | B2 * | 8/2010 | Sarin et al. | 606/130 |
| 2003/0088179 | A1 * | 5/2003 | Seeley et al. | 600/424 |
| 2003/0179856 | A1 | 9/2003 | Mitschke et al. | |

FOREIGN PATENT DOCUMENTS

| | | |
|---|---|---|
| DE | 196 39 615 | 4/1998 |
| EP | 1 380 266 | 1/2004 |

* cited by examiner

*Primary Examiner* — Tse Chen

*Assistant Examiner* — Baisakhi Roy

(74) *Attorney, Agent, or Firm* — Renner, Otto, Boisselle & Sklar, LLP

(57) ABSTRACT

A marker navigation system for detecting and displaying locations of at least two reference devices, each reference device attachable to a corresponding object includes a detection device for detecting signals emitted from the at least two reference devices, a display device for displaying the locations of the at least two reference devices and/or the objects attached to the at least two reference devices based in accordance with display signals; and a data processing device. The data processing device is configured to a) calculate locations of the at least two reference devices based on the detected signals; b) determine changes in the locations of the at least two reference devices based on the calculated locations; c) check, based on the determined changes, whether the changes in the locations of the at least two reference devices can be described by at least one checking transformation that, to a predetermined extent, transforms the locations of the at least two reference devices before the change into the locations of the at least two reference devices after the change; and d) determine the display signals for displaying the locations of the at least two reference devices and/or of objects attached to the at least two reference devices as a function of the checking result.

16 Claims, 1 Drawing Sheet

1 1a 1b CRF 2 ARF0 A ARF1 ARF2 3a 3b 20a 20b 20a' 20b' DRF 30

MARKER NAVIGATION SYSTEM FOR DETECTING AND DISPLAYING THE LOCATION OF MARKER MEANS

RELATED APPLICATION DATA

This application claims priority of U.S. Provisional Application No. 60/862,070 filed on Oct. 19, 2006, which is incorporated herein by reference in its entirety.

FIELD OF THE INVENTION

The present invention relates to a marker navigation system for detecting and displaying the location of marker means. The marker means can be attached to body structures such as, for example, bones or artificial limbs and/or to instruments, such as medical instruments.

BACKGROUND OF THE INVENTION

Conventional marker navigation systems, in particular so-called image-guided surgery (IGS) systems, generally detect and track the locations of one or more reference frames that, for example, are connected to a body structure (e.g., a bone) or to an instrument. A display of a marker navigation system typically shows only a particular region or section (e.g., a targeted region) of the operating area.

One problem with conventional marker navigation systems is that if a change occurs in the targeted region, it may be unclear whether the change was due to camera movement or to movement of the observed marker means (which for example may be connected to a body structure or an instrument).

Another problem is that large relative movements of the marker means can occur such that the objects connected to the respective marker means (e.g., the body structure or instrument), which are typically calibrated, are no longer displayed on the display (e.g., they have moved out of a display region and are "off the display"). The latter may be due to the fact that while a camera system, for example, detects a general region (e.g., the patients upper body), the surgeon may be only interested in a sub-region (e.g., a portion of the patient's chest) of the general region, and only this sub-region is displayed of the display. Thus, if the displayed objects of interest leave the sub-region (e.g., they move outside the display area), the surgeon may prefer that the display area be re-adjusted such that the objects of interest are again provided on the display.

SUMMARY OF THE INVENTION

The present invention provides a device and method that optimizes the display of marker means and/or objects connected thereto such that it is less frequently necessary to re-adjust a display area due to movement of the marker means and/or object. Further, absolute movements of a number of objects (fragments) provided with marker means can be detected and optimally displayed in a reference frame (e.g., a camera system).

Compensating for a drift in displayed objects advantageously enables the marker means and the objects connected thereto (e.g., bone fragments) to be more informatively displayed in a reference frame (e.g., a camera reference frame). In particular, this enables independent tracking of a number of fragments.

If, for example in accordance with a first scenario, a fragment A moves upwards, then the display shows that the fragment A is rising. If, in accordance with a second scenario, a fragment B moves upwards, then the display shows that the fragment B is rising. This has not been possible in accordance with the prior art. The reference frame was bound to one of the fragments A or B, e.g., fragment A was the display reference frame and remained constant or stationary in said selected representation.

The first and second scenarios then differ in that in the first scenario the fragment B drops and in the second scenario the fragment B rises. If, for example, a virtual center of mass of the fragments A and B is taken into account, even this does not enable the movement of the fragments to be displayed in a reference frame that, for example, lies in the operating theater or in the camera reference frame (lying in the operating theater).

The present invention enables the absolute movement of a number of fragments to be detected and displayed in a reference frame that lies in the camera reference frame and/or in the space in which the user is situated. Compensating for drift helps in achieving this advantage, but also represents a substantial advantage in its own right.

Marker means (e.g., a reference device such as a reference array or the like) can be detected by means of a detection means (e.g., a camera or ultrasound detector). The marker means typically comprise two to four markers that are arranged in a fixed and predetermined location relative to each other and may be mechanically connected. The markers can be passive or active markers, wherein passive markers reflect signals (e.g., waves and/or radiation) emitted in their direction, and the active markers are themselves the origin of the signals (e.g., radiation and/or waves). The signals emitted by the (active or passive) markers, which, for example, can be wave signals or radiation signals, can be detected by a detection device (e.g., the camera). In order to establish a position of the marker means relative to the detection means, the marker means may be moved to provide the detection means with various views of the marker means. On this basis, the location of the marker means relative to the detection means can be determined in a known way, in particular in a spatial reference frame. Reference is made in this respect to DE 196 39 615 A1 and corresponding U.S. Pat. No. 6,351,659, both of which are hereby incorporated by reference in their entirety.

The location of the marker means can be determined by the position of the marker means in a predetermined reference frame. The reference frame can be a reference frame in which the detection means lies. The location of the marker means can be determined by the positions of the markers, in particular the center points of the markers in the reference frame. The positions, for example, can be described using Cartesian coordinates or spherical coordinates. The location of one part (e.g., the detection means or marker means) relative to another part (e.g., the marker means) can be described by spatial angles, distances, coordinates (in a reference frame) and/or vectors, and is preferably calculated from the positions describing the location, for example by means of a program running on a computer.

The term "relative location" as used herein or the expression "location of a part A relative to a part B" thus comprises the concept of the relative positions between the two parts, in particular between the marker means and/or their markers or between a marker means (or its markers) and the detection means. In particular, centers of gravity or center points of the parts may be selected as a punctiform reference point for establishing a position. If the position of one part is known in a reference frame, then it is possible, on the basis of the relative location of two parts, to calculate the position of one of the two parts from the position of the other of the two parts.

The marker means can comprise at least two markers, and preferably three markers, and can of course also comprise more than three markers. The dimensions of the markers and the locations of the markers relative to each other may be known and available as prior known data of a data processing means, or may have been determined by a calibration process during execution of a data processing program. The shape of the markers is preferably also known.

The marker navigation system also can comprise a detection means that detects signals from the at least two markers, in particular from at least two marker means (each comprising at least two markers). As stated above, these signals may be emitted from the markers (either actively emitted by the markers or reflected by the markers from another source). In the latter case, a signal transmitting source, for example an ultrasound source or an infrared light source, can be provided that emits signals (e.g., ultrasound waves or infrared light) towards the passive markers (continuously or in pulses), wherein the passive markers reflect the signals. A data processing means, such as a computer, allows the location of the marker means relative to the detection means to be calculated, in particular the location of the marker means in a reference frame in which the detection means lies, e.g., in a reference frame that lies in an operating theater.

The data processing means can be designed to perform calculating operations, determining operations and checking operations. For example, the data processing means can calculate the locations of the marker means on the basis of the detected signals emitted from the marker means. Objects (e.g., a body structure or instruments) to which the marker means are attached are preferably calibrated. This means that relative locations at least between parts of the object and the marker means attached to the object are known and/or stored in the data processing means, such that display signals that describe the locations of the objects can be determined on the basis of the locations of the marker means. The locations of the marker means can be calculated relative to the detection means, e.g., in a reference frame in which the detection means lies. The locations can of course also be calculated in another reference frame, e.g., in a reference frame in which one of the marker means lies and/or in which the patient lies.

The patient lies in the reference frame of the detection means (e.g., the camera system) when the detection means and the patient are not moving. This assumption can be made when calculating the location of the objects. Additionally or alternatively, a marker means can be attached to the patient, for example. This can be achieved by way of example using a non-invasively attached marker means that is fixed to the patient's body and can be detected by the detection means. One example of this is a so-called "headband", in particular an "ENT headband", which can be attached to various points on the patient's body, for example on the extremities, by means of a band. A marker means can also be attached to the couch surface, in particular the table, on which the patient is lying. The physician also can be selected as a reference frame, for example, by providing the physician with a marker means (e.g., a headband). Lastly, the treatment room, e.g., the operating room, also can be selected as a reference frame. To this end, marker means, for example, can be fixedly connected to the room, e.g., to the wall or walls.

The detection means may be designed to determine changes in the locations of the marker means, and also changes in the reference frame of the detection means. The changes can be determined on the basis of the calculated locations and may be determined, for example, between particular time intervals. This means, for example, that at particular time intervals the detection means checks whether the calculated locations of the marker means have changed.

Instead of checking at particular intervals, a change in location may be constantly checked and, once it is established that a change has occurred, then the extent of that change may be determined. The changes in the location of the marker means, for example, can be described by vectors in the reference frame of the detection means.

It also may be established whether determined changes in the location of the marker means can be attributed to a relative movement of the marker means or whether it only appears to have been caused by a change in the location of the detection means and/or by a change in the location of an object coupling the movement (called a coupling object below). An example of an object or coupling object is the patient or a couch on which a patient is lying. The coupling object can be characterized in that the marker means have a stationary relationship with respect to the coupling object if no external force acts on the marker means or the objects connected to them.

It then may be determined whether the determined changes in the locations of the marker means were caused by a movement of the detection means or the coupling object. To this end, it may be determined whether the changes in the locations of (each of the marker means can or could be displayed by a (single) transformation, in particular a transformation matrix, which describes a change in the location of the detection means or a coupling object. In particular, it may be determined whether the changes in location can be described by translating and rotating the reference frame in which the detection means lies. In particular, it also may be determined whether the changes in location can be described by rotating and/or translating a reference frame (ARF0) in which the marker means were lying before the change. The rotation and/or translation of the reference frame ARF0 can be likewise described by a transformation, such as a transformation matrix. This can be performed by means of numerical methods, with the aid of which a center point of rotation can be determined. The aforementioned coupling object can be characterized in that it lies in the reference frame ARF0.

In the case of a translational movement due to a change in the location of the detection means or the coupling object, it will be seen that the determined changes in the location of the marker means and/or the reference frames assigned to them (ARF1, ARF2) can be described by the same vector. A rotational movement of the coupling object or the detection means can be detected by determining a center point of the rotation and a rotational transformation (rotation matrix) that are identical for all the marker means and/or assigned reference frames (ARF1, ARF2).

The data processing means can be configured to check the changes (changes in location), wherein the processing means checks whether the changes in location (in particular all the changes in location) can or could be described and/or explained by a (single) transformation. If this is the case, a positive checking result may be assumed. This transformation is referred to here as the "checking transformation". The checking transformation may cause a translation, a rotation, or a combination of a translation and a rotation.

A checking transformation can, but need not, be determined. It is also sufficient to establish, using mathematical methods, whether the changes in location could be described or at least described to a predetermined extent by a (single) transformation (checking transformation). If the changes could be (at least substantially) described by a (single) checking transformation, then a positive checking result can be assumed.

A positive checking result also can be obtained without determining a checking transformation. This can be achieved, for example, as follows. Two of the marker means can be selected and designated as a first and second marker means. A relative transformation can be determined that transforms a first marker reference frame, in which the first marker means lies, into a second marker reference frame, in which the second marker means lies. It then can be observed and determined whether said relative transformation changes in the course of time, and if so, to what extent. If, for example, said relative transformation remains constant, then a positive checking result may be assumed. This means that even if the location of the first marker means and the second marker means changes, for example in a camera reference frame (in which the camera is lying), this change can be attributed to a coupled movement of the first marker means and the second marker means, since the relative transformation remains the same. The result of this is that both the change in the location of the first marker means and the change in the location of the second marker means in the camera reference frame could be described by the same checking transformation. A positive checking result is thus obtained, without it being necessary to specifically calculate the checking transformation.

It is sufficient to calculate the aforesaid relative transformation. The extent of the change in the relative transformation, for example, can be established by determining a relative transformation at a first point in time and describing it using a matrix. This matrix can be multiplied by the inverse of a second matrix, wherein the second matrix describes the relative transformation at a second point in time. If the result of the multiplication is a matrix that is similar to the unit matrix, then it may be assumed that the relative transformation has not significantly changed from the first point in time to the second point in time.

In order to obtain a measure of the similarity of the relative transformations at the first and second points in time, the difference between the aforesaid matrix multiplication and a unit matrix can be formed. The elements of the resulting matrix then can be examined as to their magnitude. The maximum value of the elements, for example, can be picked out and compared with a threshold value. If it is smaller than the threshold value, then it is assumed that the change in the relative transformation is minor, e.g., a positive checking result is obtained. Alternatively, the magnitudes of the elements of the differential matrix can be added and compared with a threshold value. Other methods such as forming squares are likewise possible. The relative transformation preferably describes at least one translation and/or rotation.

If there are more than two marker means, then it is possible to determine a relative transformation between each of the two marker means. Then, for example, it may be assumed that a positive checking result is obtained if no changes or only minor changes are seen in the course of time for a particular relative transformation, a number of particular relative transformations, or all the relative transformations that respectively link two reference frames of two marker means.

A checking transformation can be determined, for example, using numerical methods. The checking transformation also may be determined when applying the checking transformation in the reference frame of the detection means (CRF). This as has the result of the locations of (in particular each of) the marker means relative to the detection system before the determined changes in location can be transferred into the new locations of (in particular each on the marker means after the determined changes in location using the checking transformation. In order to discover a checking transformation, a first transformation, for example, can be determined that describes the change in the location of a first marker means. A second transformation then can be determined that describes the change in the location of a second marker means. The first transformation, for example, then can be interpreted as a checking transformation and compared with the second transformation. If the checking transformation (the first transformation) matches or at least substantially matches the second transformation, then a positive checking result can be determined.

The same applies if a checking transformation can be found that can transfer the locations of the marker means in a common reference frame ARF0 before the determined changes (changes in location) into the locations after the determined changes (changes in location). In other words, if the locations of the marker means in the reference frame CRF or ARF0 are subjected to the checking transformation, then if a checking result is positive, then a compensation is made to the changes in the location of the marker means in the reference frame CRF or ARF0, e.g., the locations of the marker means are returned back to their initial locations (before the changes).

The above-mentioned checking transformation has been considered with regard to each of the marker means. In an alternative embodiment, a predetermined group can be selected from the detected marker means and only a coupled movement of this group checked, for example, by only determining relative transformations between marker means of this group and examining how they change over time. Said group of marker means, for example, can be a group of marker means that are fixedly connected to the patient, while still other marker means, which may not be fixedly connected to the patient and with respect to which detecting a coupled movement is not of interest, can be detected by the detection means. Thus, it may be checked whether the change in the location of a particular group of detected marker means can or could be described by a checking transformation.

Applying the checking transformation has been described above such that it is applied in a reference frame (CAF or ARF0) to the locations (which are for example described by coordinates). Alternatively, this can of course also be envisaged such that the checking transformation is applied to the respective reference frame (CAF or ARF0), such that the coordinates for the marker means (for example by rotating the reference frame) are again the same as those which were obtained before the determined changes in location.

Determination of the checking transformation can include some uncertainties, or the determined changes in the locations of the marker means may have been substantially, though not exclusively, caused by a movement of the detection means or the coupling object. This means that there also can be a certain degree of relative movement between the marker means.

As stated above, a positive checking result may be established if the changes in location can be attributed to a movement of the detection means and/or the coupling object. For the aforesaid reasons, a positive checking result also can be established when (all of) the changes in location can be (at least) substantially described by a (single) checking transformation. In order to quantify the word "substantially" for data processing by the data processing means, a checking transformation is preferably determined that, once applied, results in the smallest possible deviation between the locations of the marker means before the determined changes and the locations of the marker means after the determined changes. The marker means for which the largest deviation occurred, for example, can be selected for quantification. A first deviation between the first location (the location before the determined change) and the second location (the location after the determined change and after the checking transformation for compensating for the change in location has been applied) can be quantified, for example, by the distance between the first and second location. A second deviation also can be determined as the difference between the first location (the location before the determined change in location) and a third location (the location after the determined change in location and without a checking transformation being applied). The first deviation then can be related to the second deviation. If this relationship is smaller than a predetermined percentage, then the checking result may be regarded as being positive. The predetermined percentage, for example, can measure less than 50%, 25%, 10%, 5% or 1%. If the criterion "less than a predetermined percentage" is fulfilled, then it is assumed that the changes in the locations of each of the marker means can be described at least to a predetermined extent by the checking transformation.

As an alternative to or in addition to forming the aforesaid relationship, the cited criterion "substantially" can also be quantified by absolute threshold values. If, for example, the first deviation is smaller than a pre-set threshold value, it can be assumed that the checking result is positive, e.g., the change in location can be substantially described by the checking transformation. Alternatively or additionally, a positive checking result can be assumed when the second deviation is above a particular threshold value. In particular, a number of first threshold values can be established for the first deviation and a number of second threshold values can be established for the second deviation in the aforesaid sense, wherein each first threshold value can be assigned to a second threshold value (e.g., in the form of a table), and a positive checking result can be assumed when the first deviation falls below the first threshold value and the second threshold value is exceeded by the second deviation.

Display signals that show the locations of the marker means and/or the objects connected to the marker means relative to a display reference frame can be determined as a function of the checking result. This means that if a checking result is positive, the detected changes in location are not further processed and the present display signal transmitted to the display means is retained.

Determining display signals as a function of the checking result does not exclude also determining the display signals as a function of other (optional) conditions. These conditions can include whether the objects displayed before the change in location could also be seen after said change in location has been displayed on a display means (e.g., a screen). Another optional condition, as a function of which the display signals can be determined, can also be represented by the speed of the change in location. The speed can be calculated from the extent of the change in location (i.e., the distance between the aforementioned first location and third location) divided by the time in which the change in location occurred. It is for example possible to only display changes in locations that occur at a speed which is above or below a particular speed threshold value.

Alternatively or additionally, changes in location can be prevented from being displayed if the changes in location occur at a speed that is above a first speed threshold value and/or below a second particular speed threshold value. The aforesaid conditions can be used, for example, such that only rapid changes in location are displayed, provided only such rapid changes are of interest to the surgeon. Alternatively, the rapid changes in location can be suppressed if, for example, they represent a movement that is caused by vibrations and is a distraction to the surgeon.

Thus, changes in the locations may not be displayed by the display means, in particular as a function of the checking result (and optionally also as a function of other conditions). This can be implemented by the data processing means by leaving the display signals unchanged. Alternatively, the display area or the reference frame of the display in which the marker means and/or the objects connected to them are displayed can be subjected to the determined checking transformation, such that a change is not seen on the display or only those changes are shown that are not compensated for by applying the checking transformation. The result of the latter is that if there is an overlap of a relative movement between the marker means and a movement of the detection means and/or the coupling object, (only) the relative movement is shown, whereas the changes due to the movement of the detection means and/or the coupling object are not shown.

Thus, if the checking result is positive, the usual processing of the detection signals is changed. The usual representation may be retained even when a checking result is positive, but only as long as predetermined objects (which for example have hitherto been displayed by the display means) continue to remain visible on the display means.

It can occur, for example, that a drift is not completely compensated. The cause of this can be numerical inaccuracies or the aforesaid conditions, if compensations are made for only changes in location at speeds which are within a predetermined range of speeds. Another cause of the predetermined objects leaving the display area can be absolute movements of (all the) displayed objects in one direction. For the aforesaid scenarios, it thus can occur that at least one of the displayed objects moves out of the visible range, e.g., is only partially displayed. The displayed objects then can be re-aligned, in particular centered, such that all the objects are completely displayed by the display means. To this end, the data processing means can be designed such that it sets a constant minimum distance from the displayed objects to the edge of the displayed area. In other words, re-centering can keep the minimum distance from each object to the edge of the display area constant. The displayed objects can be manually re-aligned by the operator or also automatically re-aligned, where in the latter case, the re-alignment may be indicated to the operator by a warning signal.

The data processing means also can be configured to determine the checking transformation as follows. For each detected object, at least for each object displayed on the display means, a transformation can be calculated that is referred to here as a change transformation. The change transformation transforms the first location (before the change) into the third location (after the change) for each object. The change transformation can be performed in the reference frame ARF0 in which the reference frames of the (displayed) objects lay before the change.

In a subsequent step, the change transformations for the individual (displayed) objects then can be compared with each other. If the change transformations are the same, a positive checking result can be established. A positive checking result also can be established if the change transformations are similar to a predetermined degree or extent. The latter means that when one of the determined change transformations is applied to the first location of all the displayed objects, a location can be respectively obtained that only deviates to a minor extent from the third location (after the change in location) for each object. A minor extent means that the relationship of the deviation relative to the extent of the change in location is smaller than a predetermined percentage. The predetermined percentage measures for example 25%, 10%, 5% or 1%.

The data processing means can determine the checking transformation from the change transformations determined for the respective displayed objects, for example, by averaging the change transformations or by selecting one of the change transformations.

As already mentioned above, it is possible to calculate a speed of the change. To this end, the distance between the third location (after the change) and the first location (before the change) can be calculated for an object, and divided by the time in which said change in location occurs. If the speed is below a pre-set value, then if a checking result is positive, a change in the locations is preferably not displayed. If the speed is equal to or above the threshold amount, then the detected change in location is preferably displayed. The threshold value for the speed is for example above 0.1 mm/s, 1 mm/s, 3 mm/s or 1 cm/s and/or preferably below 10 cm/s, 3 cm/s, 1 cm/s, 1 mm/s. In this way, it is possible to eliminate a slow drift of the displayed objects.

The change in location may not displayed when the speed is above the threshold value, even if otherwise (i.e., when the change in location is displayed), at least one of the displayed objects would at least partially leave the displayed area.

BRIEF DESCRIPTION OF THE DRAWINGS

The forgoing and other features of the invention are hereinafter discussed with reference to the drawing.

DETAILED DESCRIPTION

Figure 1:
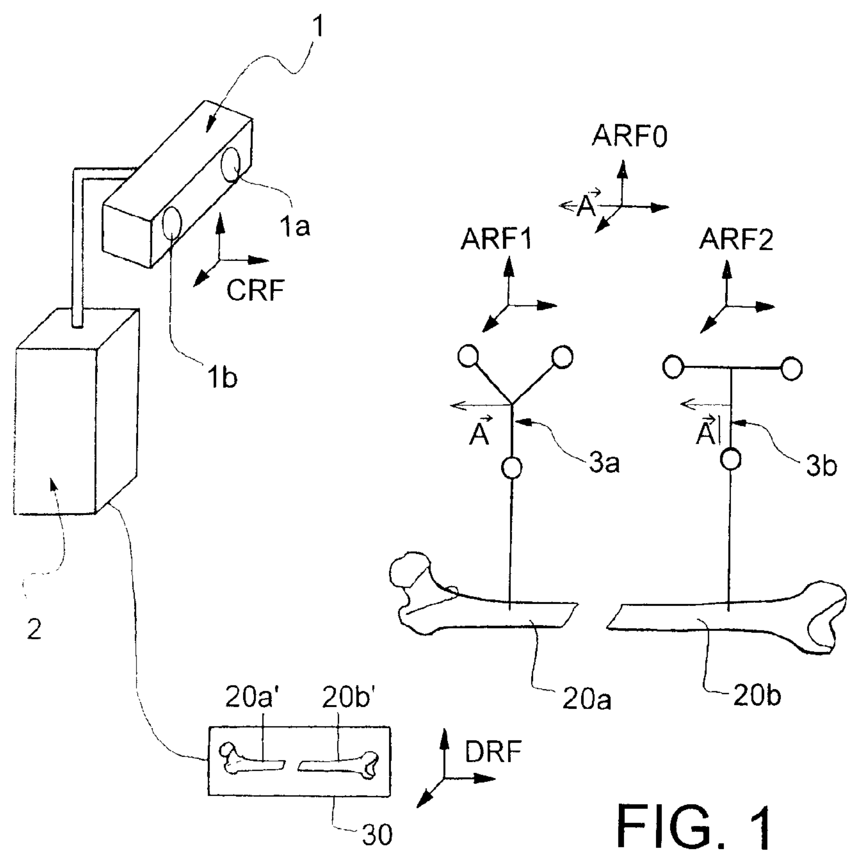
FIG. 1 shows an exemplary marker navigation system in accordance with the invention.

FIG. 1 shows an exemplary marker navigation system in accordance with the invention, wherein reference stars 3*a* and 3*b* are attached bone parts 20*a* and 20*b*, respectively, and wherein the bone parts can be moved relative to each other. The reference stars 3*a* and 3*b* are each an example of a marker means and comprise three marker spheres arranged in characteristic locations relative to each other.

A camera 1 is also provided that serves as a detection means. The camera 1, which is connected to a data processing means 2 (e.g., a computer) via a data signal line, comprises detection elements 1*a* and 1*b*. A camera reference frame (CRF) is assigned to the camera 1, a reference frame ARF1 (array reference frame) is assigned to the reference star 3*a*, and a reference frame ARF2 is assigned to the reference star 3*b*. The camera 1 lies in the reference frame CRF, the reference star 3*a* lies in the reference frame ARF1, and the reference star 3*b* lies in the reference frame ARF2. The two detection elements 1*a* and 1*b*, with the aid of the data processing means 2, are preferably provided to enable (in a manner similar to human spatial perception) a calculation of the location of the reference stars 3*a* and 3*b* relative to the detection means 1 based on a detection signal.

When using the marker navigation system of FIG. 1, the following situation can then occur. A location of the reference stars 3*a* and 3*b* is not changed, but a location of the camera 1 is changed. If the change in the camera location is not taken into account, the display of the bone parts 20*a*' and 20*b*' on a display 30 changes, even though the bone parts 20*a* and 20*b* have not actually moved. Another, comparable situation, for example, is when the patient is moved while lying on a support base (the coupling object). These movements can mean that the bone parts 20*a*' and 20*b*' disappear from the displayed area of the display 30. The latter also may be undesirable.

To compensate for the above, a movement of the camera 1 and/or a coupling object (e.g., the patient or couch) is deduced when such detected movement can be explained by a movement of the camera 1 and/or the coupling object. The reference frame ARF0 shown in FIG. 1 is connected to the coupling object.

If, for example, a shift in each of the reference stars 3*a* and 3*b* by the same vector A is detected in FIG. 1, this can be explained by a shift in the patient or for example the support surface (on which the patient is lying). In this case, it is possible to prevent such shift from being displayed. This can be achieved, for example, by not changing the display signals transmitted from the data processing means 2 to the display 30, despite the detected change. Alternatively, the display reference frame CRF (i.e., the camera reference frame) can likewise be shifted by the vector A, such that there is no change in the position of the bones 20*a*' and 20*b*' in the reference frame CRF and thus also no change to be seen on the display 30.

Using numerical methods, it can be ascertained from the detected change in the reference stars 3*a* and 3*b* whether said change can be described by a transformation matrix, wherein the transformation matrix can be described by a translation or rotation of the reference frame CRF or a reference frame ARF0. The reference frames of the reference stars (here the reference frames ARF1 and ARF2 before the change) lie in the reference frame ARF0.

A check as to whether the changes in the location of two marker means could be described by a (single) checking transformation, for example, can be made as follows. In a specific implementation, the positions of two marker arrays A and B are detected in camera coordinates, wherein the positions are expressed by coordinate transformations $M_A$ and $M_B$ from the reference frame of the camera to the respective reference frame A or B. The coordinate transformations can be substantially represented by 4×4 matrices, and generally contain a degree of rotation and a degree of translation.

At an initial point in time $t_0$, the coordinate transformations $M_A(t_0)$ and $M_B(t_0)$ are detected and stored. In addition, an initial relative coordinate transformation $M_{BA',last}$ is stored. At consecutive points in time $t_i$, the coordinate transformations $M_A(t_i)$ and $M_B(t_i)$ are detected again, from which the relative coordinate transformation $M_{BA}(t_i)$ is ascertained.

Then an initial check is performed to determine whether there is a coupled movement of the arrays A and B, by forming a "differential matrix" from the ascertained relative coordinate transformations:

$$\Delta M_{BA}(t_i)=M_{BA}(t_i)*(M_{BA',last})^{-1}-1_4$$ (the latter is the four-dimensional unit matrix)

The criterion for a couple movement and therefore for a positive checking result is that the difference between consecutive relative positions is very small. Mathematically, for example, this can be interpreted such that the maximum norm of the calculated differential matrix must be smaller than a pre-set absolute threshold value:

$$\|\Delta M_{BA}(t_i)\|\max<\text{threshold value}$$

That is, the element of the matrix having the highest value must be smaller than the threshold value. Next, the value of $M_{BA}(t_i)$ is assigned to the matrix $M_{BA',last}$, such that at the point in time $t_{i+1}$, it is again possible to refer to the previous relative position.

If a coupled movement has been identified (i.e., if the checking result is positive), then such movement is suppressed on the display 30 of the marker means. As a result, none of the marker means and/or none of the bodies connected to the marker means are moved on the display 30.

If there is no coupled movement, then each of the marker means A and B is moved on the display 30 in the way said movement is represented in the camera system. To this end, the relative shift in the position is individually calculated for each marker array, in a similar way to above, by comparing it with the position from the previous step in time. If there previously was a coupled movement, then the position was not stored again so as to enable only the non-coupled movement to be displayed.

Figure 2:
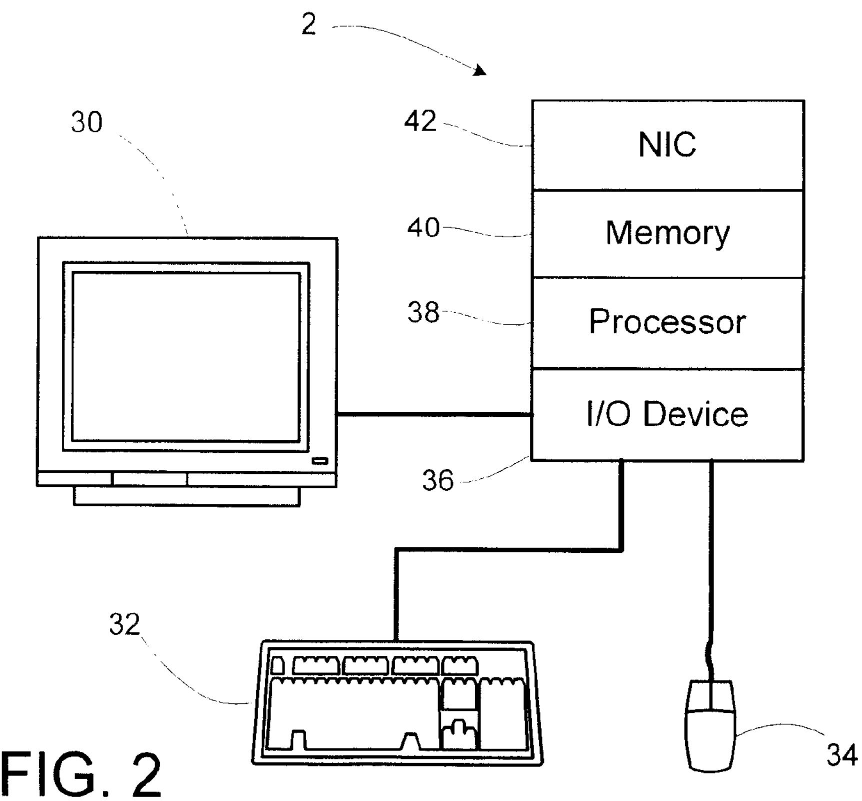
FIG. 2 is a block diagram of an exemplary computer system that may be used to carry out one or more of the methods described herein.

Moving now to FIG. 2 there is shown a block diagram of an exemplary computer 2 that may be used to implement one or more of the methods described herein. The computer 2 may include a display 30 for viewing system information, and a keyboard 32 and pointing device 34 for data entry, screen navigation, etc. A computer mouse or other device that points to or otherwise identifies a location, action, etc., e.g., by a point and click method or some other method, are examples of a pointing device 34. Alternatively, a touch screen (not shown) may be used in place of the keyboard 32 and pointing device 34. The display 30, keyboard 32 and mouse 34 communicate with a processor via an input/output device 36, such as a video card and/or serial port (e.g., a USB port or the like).

A processor 38, such as an AMD Athlon 64® processor or an Intel Pentium IV® processor, combined with a memory 40 execute programs to perform various functions, such as data entry, numerical calculations, screen display, system setup, etc. The memory 40 may comprise several devices, including volatile and non-volatile memory components. Accordingly, the memory 40 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 38 and the memory 40 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 42 allows the computer 2 to communicate with other devices.

A person having ordinary skill in the art of computer programming and applications of programming for computer systems would be able in view of the description provided herein to program a computer 2 to operate and to carry out the functions described herein. Accordingly, details as to the specific programming code have been omitted for the sake of brevity. Also, while software in the memory 40 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A marker navigation system for detecting and displaying locations of at least two reference devices, each reference device attachable to a corresponding object, comprising:

a detection device for detecting signals emitted from or reflected by the at least two reference devices;

a display device for displaying, based in accordance with display signals, the locations of the at least two reference devices and/or the objects attached to the at least two reference devices; and a data processing device configured to a) calculate the locations of the at least two reference devices based on the detected signals;

b) determine changes in the locations of the at least two reference devices based on the calculated locations;

c) check, based on the determined changes, whether the determined changes in the locations of the at least two reference devices can be described by a same checking transformation that, to a predetermined extent, transforms the locations of the at least two reference devices before the change into the locations of the at least two reference devices after the change; and d) determine the display signals for displaying the locations of the at least two reference devices and/or of objects attached to the at least two reference devices as a function of the checking result.

2. The device according to claim 1, wherein the object is a medical instrument.

3. The marker navigation system according to claim 1, wherein the data processing device is configured to set a positive checking result when at least one relative transformation does not change or changes less than a predetermined extent over time, wherein said at least one relative transformation transforms a transformation from a first reference device reference frame in which a first reference device of the at least two reference devices lies into a second reference device reference frame in which a second reference device of the at least two reference devices lies.

4. The marker navigation system according to claim 3, wherein if the checking result is positive, the data processing device is configured to not include or only partially include the determined changes in the display signals.

5. The marker navigation system according to claim 3, wherein if the checking result is positive, the data processing device is configured to retain the display signals that do not reflect the determined changes.

6. The marker navigation system according to claim 3, wherein if the checking result is positive, the data processing device is configured to calculate a speed of the changes and, if the calculated speed is less than or greater than a predetermined speed, then the display signals are unchanged or the display signals are determined such that the determined changes are not displayed or are only partially displayed.

7. The marker navigation system according to claim 6, wherein if the calculated speed is greater than or equal to the predetermined speed, the data processing device is configured to not display or partially display the determined changes, and if the locations that have changed in accordance with the determined changes are displayed, all the previously displayed locations are not displayed on the display device.

8. The marker navigation system according to claim 1, wherein if a checking result is positive, the data processing device is configured such that the locations of the at least two reference devices after the change in location are subjected to a transformation that at least partially reverses the change in the location, and the display signals are calculated on the basis of the transformed locations.

9. The marker navigation system according to claim 8, wherein the transformation corresponds to or is calculated from the at least one checking transformation.

10. The marker navigation system according to claim 1, wherein if the checking result is positive, the data processing device is configured to leave the display signals unchanged, such that the display device does not display any change in the locations or the determined changes are only partially displayed and/or the changed and determined locations are subjected to the checking transformation before determining the display signals, such that the changes are at least partially reversed.

11. The marker navigation system according to claim 1, wherein the data processing device is configured to determine the at least one checking transformation based on the assumption that:

a) the determined changes have been caused by rotating and/or translating the detection means; and/or b) the determined changes have been caused by rotating and/or translating an object that is stationary relative to the at least two reference devices.

12. The marker navigation system according to claim 1, wherein the data processing device is configured to:

determine the at least one checking transformation by calculating for each of the at least two reference devices a change transformation that describes the change in the location from before the change to after the change;

compare the calculated change transformations with each other; and establish a positive checking result if all the change transformations are within a predetermined range of one another.

13. The marker navigation system according to claim 12, wherein the data processing device is configured to determine the at least one checking transformation from the change transformations.

14. The marker navigation system according to claim 1, wherein the at least two reference devices are each attached to respective different object, the respective different objects movable relative to each other.

15. A method for detecting and displaying a location of at least two reference devices via a marker navigation system, wherein each reference device is attachable to a corresponding object, comprising:

detecting signals emitted from or reflected by the at least two reference devices;

calculating locations of the at least two reference device based on the detected signals;

determining changes in the locations of the at least two reference devices based on the calculated locations;

checking, based on the determined changes, whether the changes in the location of each of the at least two reference devices can be described by a same checking transformation that at least to a predetermined extent transforms the locations of the at least two markers before the change into the locations of the at least two markers after the change;

determining, as a function of the checking result, display signals that display the locations of the at least two markers and/or objects attached to the at least two markers;

displaying the locations in accordance with the display signals.

16. The method according to claim 15, wherein the at least two reference devices are each attached to a respective different object, the respective different objects movable relative to each other.

* * * * *